(12) United States Patent
Rho et al.

(10) Patent No.: US 6,521,662 B2
(45) Date of Patent: Feb. 18, 2003

(54) CERAMIDE-LIKE COMPOUNDS HAVING ANTIOXIDANT PROPERTY AND A METHOD FOR PREPARATION THEREOF, AND A COSMETIC COMPOSITION CONTAINING THE SAME

(75) Inventors: Ho Sik Rho, Euiwang-shi (KR); Duck Hee Kim, Seoul (KR); Kil Joong Kim, Suwon-shi (KR); Jae Won You, Seoul (KR); Hak Hee Kang, Seongnam-shi (KR); Ok Sub Lee, Anyang-shi (KR); Jong Ho Park, Yongin-shi (KR); Su Sun An, Seoul (KR); Eui Dong Son, Suwon-shi (KR)

(73) Assignee: Pacific Corporation, Seoul (KR)

( * ) Notice: Subject to any disclaimer, the term of this patent is extended or adjusted under 35 U.S.C. 154(b) by 0 days.

(21) Appl. No.: 09/764,426

(22) Filed: Jan. 19, 2001

(65) Prior Publication Data

US 2001/0056083 A1 Dec. 27, 2001

(30) Foreign Application Priority Data

Apr. 28, 2000 (KR) .......................................... 2000-22835

(51) Int. Cl.[7] ......................... A61K 31/355; A61K 6/00; A61K 31/74; A01N 33/08; C11C 3/00
(52) U.S. Cl. ...................... 514/458; 514/669; 424/401; 424/78.03; 554/61
(58) Field of Search ............... 424/401, 78.03; 514/669, 458; 554/61

(56) References Cited

U.S. PATENT DOCUMENTS 5,198,210 A * 3/1993 Critchley et al. ........ 424/78.03
5,723,497 A * 3/1998 Ohashi et al. ............... 514/669
6,060,612 A * 5/2000 Hong et al. .................... 554/61

FOREIGN PATENT DOCUMENTS

| EP | 0 798 305 A1 | 10/1997 |
|---|---|---|
| FR | 2757853 A1 | 7/1998 |
| JP | 63-243016 A | 10/1988 |
| KR | 1998-053299 A1 | 9/1998 |
| KR | 1998-053300 A1 | 9/1998 |
| KR | 1998-053301 A1 | 9/1998 |
| KR | 1998-054693 A1 | 9/1998 |
| KR | 1999-010145 A1 | 2/1999 |
| KR | 1999-011436 A1 | 2/1999 |
| WO | WO 93/02661 A1 | 2/1993 |

* cited by examiner

Primary Examiner—Sreeni Padmanabhan
Assistant Examiner—Michael A Willis
(74) Attorney, Agent, or Firm—Sughrue Mion, PLLC

(57) ABSTRACT

A ceramide-like compound having properties of the natural ceramides are represented by the following formula (I), and a method for producing the same, and a cosmetic composition containing the same as an active ingredient:

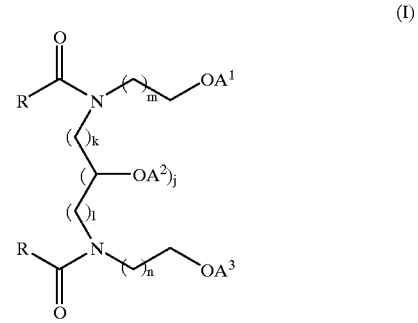

(I)

18 Claims, No Drawings

CERAMIDE-LIKE COMPOUNDS HAVING ANTIOXIDANT PROPERTY AND A METHOD FOR PREPARATION THEREOF, AND A COSMETIC COMPOSITION CONTAINING THE SAME

BACKGROUND OF THE INVENTION

1. Field of the Invention

The present invention relates to a ceramide-like compound having properties of the natural ceramides, and to a method for producing the same, and to a cosmetic composition containing the same as an active ingredient.

2. Related Arts

To maintain its life action, an organism needs protective barrier which prevents noxious foreign materials including microorganisms from external penetration, and counteracts the loss of body fluids such as water and blood. In case of human beings, stratum corneum, the outermost layer of the epidermis, serves as this protective barrier. The stratum corneum prevents water within the skin from excessive evaporation, and controls penetration of foreign materials.

Dead, flat-shaped cells, corneocytes filled with keratin are embedded in the lipids of the intercellular domains to form membraneous bilayers. The corneocytes and the intercellular lipids make up the so-called permeable barrier. The intercellular space of the stratum corneum is mainly composed of glycolipids, cholesterol, free fatty acids and ceramides. Among them, the ceramides play an important role in maintaining well-balanced water content which is involved in skin elasticity, appearance and barrier functions.

However, skin aging or skin damage caused by detergents which remove the lipids essential for the barrier function may disturb lipid synthesis and reduce ceramide content in the stratum corneum. Thus, cell cohesion may be weak and the stratum corneum cannot serve as protective barrier. The skin may lose elasticity. As the ceramide content decreases, transepidermal water loss, direct exposure to exterior irritation such as UV or chemicals, and peeling off of the stratum corneum may occur and thus the skin may be rough and damaged.

It has been reported that external application, such as cosmetics or pharmaceutical application, of ceramides can recover the lamella structure disturbed by skin aging or damage of the stratum corneum. Thus, stratum corneum can fully function as protective barrier.

For the purpose of external application of ceramides, efforts have been made to find natural ceramide in animals, plants and microorganisms. As a result, various animals, plants and microorganisms containing natural ceramides were discovered. However, ceramide of natural origin is scarce, and it is difficult to isolate highly pure ceramides. Thus, supplies of natural ceramides by extraction thereof increase manufacturing cost and the price of final product. In addition, natural ceramides have low solubility in various organic solvents widely used in cosmetics. That is to say, only a small quantity of ceramides can be used in cosmetics, hindering their primary effects to an insufficient level.

The present inventors have conducted extensive studies on the molecular structure of natural ceramides in order to synthesize ceramide-like compounds which are structurally similar to natural ones. Natural ceramides have two long chain alkyl groups, amides, and hydroxyl groups. Considering this structural feature, molecular design was performed to synthesize ceramide-like compounds having two long chain alkyl groups, one or more amides and hydroxyl groups.

Because skin ceramides form a stable lamella layer in the stratum corneum for their function as the skin barrier, ceramide-like compounds should be also easily delivered into the intercellular space of the stratum corneum. Under this consideration, the present inventors introduced phosphoric or sulfuric group into the ceramide-like structures. The phosphate or sulfate group enhances the penetration through the skin surface. They are removed easily by enzymes, then transformed into more stable lipophilic form.

Further, the present inventors introduced a tocopheryl group as a hydrophobic group into the ceramide-like structures in order to prevent the biological membranes from oxidation. That is to say, a tocopheryl group is introduced into the ceramide-like structures since it has an excellent compatibility in the living body and anti-oxidation, action although the unstable property of tocopherol has limited the uses of tocopherol as a cosmetic source.

SUMMARY OF THE INVENTION

Thus, the purpose of the present invention is to provide new ceramide-like compounds represented by the following Formula (I):

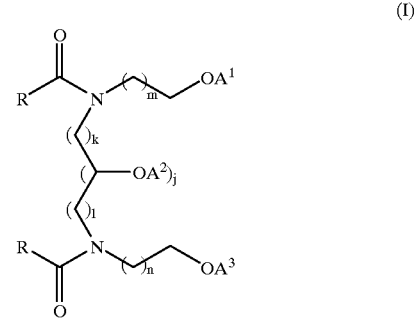

wherein, m and n, which may be the same or different, each is independently an integer from 1 to 3, , inclusive;

k and l, which may be the same or different, each is independently an integer from 1 to 2, inclusive;

j is 0 or 1;

$OA^1$, $OA^2$ and $OA^3$, which may be the same or different, each represents OH or any one of the following structures: and

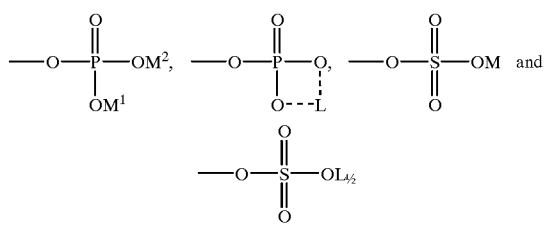

(wherein,

M, $M^1$ and $M^2$ represent independently alkali metals or organic base containing nitrogen, and L represents alkaline earth metals.)

R represents a group having the following structure:

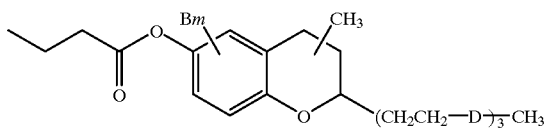

wherein,

B is methyl group at the 5-,7- or 8- position;

m is an integer from 1 to 3, inclusive; and

D is —$CH_2$—$CH(CH_3)$— or —CH=$C(CH_3)$—.

Further, other object of the present invention is to provide a method for preparing the ceramide-like compounds (I).

Also, still other object of the present invention is to provide cosmetic compositions containing the ceramide-like compounds (I) as an active ingredient.

The above and other objects and features of the present invention will be apparent to the skilled in the art from the following detailed description.

DETAILED DESCRIPTION OF THE INVENTION

The method of preparation of the compounds (I) according to the present invention will be described in more detail.

(1) reacting primary amino alcohol with dihalo compound or monohalo epoxy compound in alcohol under an inert atmosphere, to produce secondary amino alcohol derivative represented by the Formula (II):

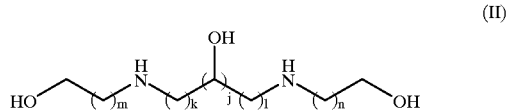

(II)

wherein, j, k, l, m and n have the same structural features as defined in Formula (I), respectively;

(2) reacting the secondary amino alcohol derivative of step (1) with tocopherylsuccinic acid chloride in the presence of an alkali or organic base to produce the diamide compound;

(3) dissolving the diamide compound of step (2) in an organic solvent, and filtering off the precipitates. After evaporating off the solvent, then recrystallizing the residue in organic solvents;

(4) phosphorylating or sulfating the diamide compound obtained in step (3);

(5) neutralizing the product of step (4) with alkali or base.

In detail, the primary amino alcohol employed in step (1) include ethanolamine, 3-amino-1-propanol and 4-amino-1-butanol and the dihalo compounds employed in step (1) include 1,3-dichloro-2-propanol, 1,3-dibromo-1-propanol, 1,2-dichloroethane and 1,2-dibromoethane. The monohalo epoxy compounds include epichlorohydrin, epibromohydrin, 3,4-epoxy-1-chlorobutane, 3,4-epoxy-1-bromobutane, 4,5-epoxy-1-chloropentane, and 4,5-epoxy-1-bromopentane.

Further, the alkali catalysts employed in step (2) include potassium hydroxide, sodium hydroxide, magnesium hydroxide, calcium hydroxide, sodium carbonate, potassium carbonate, magnesium oxide and calcium oxide. The organic bases include triethanolamine and pyridine. The tocopherylsuccinic acid chloride may be obtained from synthetic or natural tocopherol. It is prepared by reacting a tocopherylsuccinic acid with a chloride such as thionyl chloride. And tocopherylsuccinic acid is obtained by reacting a succinic anhydride with a tocopherol having a type such as α, β, γ, δ and ε.

The organic solvents employed in step (3) include alcohols such as methanol, ethanol, propanol and isopropanol; halo compounds such as dichloromethane, chloroform, 1,2-dichloroethane and carbon tetrachloride; hydrocarbons such as n-hexane, cyclohexane, benzene and toluene.

The phosphorylating reagents employed in the step (4) include phosphorus oxychloride and phosphoric anhydride. The sulfating reagents include chlorosulfonic acid and sulfur trioxide.

Further, the neutralizing agents employed in the step (5) include alkali metal or alkali earth oxides such as sodium hydroxide, potassium hydroxide, calcium hydroxide, magnesium hydroxide, calcium oxide and magnesium oxide; basic amino acids such as lysine, arginine and histidine; ammonia or amines such as triethanol amine; cationic polymers such as polyquaternium-4, -6, -7, -10, -11 and -16; and cationic surfactants such as lauryldimethylbenzylammonium chloride and stearyldimethylbenzyl ammonium chloride.

The ceramide-like compounds (I) prepared by the above method may protect the skin from external irritations and have skin tonicity and recuperation ability. Since these compounds exhibit good affinity to the stratum corneum, they make the lamella structure denser with various lipids including cholesterol and fatty acids within the intercellular space of the stratum corneum, thus increasing the moisture retention ability. Further, the compounds once absorbed into the stratum corneum may be decomposed by enzymes to release tocopheryl group, and thus prevent the aging of biological membranes. Also, the compounds may be decomposed by enzymes to release phosphoric or sulfuric group. The decomposed compounds have lower solubility than the original compounds, and thereby can be stabilized within the lamella structure together with various lipids.

Therefore, these ceramide-like compounds of the present invention are useful as a cosmetic active ingredient. The ceramide-like compounds of the present invention may be incorporated in the epidermal composition such as cosmetic composition. The composition may contain the ceramide-like compounds in the amount of 0.001~20% by weight, preferably 0.1~10% by weight, which can be chosen depending on the formulations or the final purposes of the composition. Further, the composition containing the ceramide-like compounds of the present invention may be formulated, but not limited thereto, skin softeners, astringents, nutrient toilet water, nutrient creams, massage creams, essences, eye essences, eye creams, cleansing creams, cleansing foams, cleansing water, packs, powders and the like.

PREFERRED EMBODIMENT OF THE INVENTION

The present invention will be described in more detail by way of the following examples. However, these examples are provided for only illustration purpose and should not be construed as limiting the scope of the invention, which is properly delineated in the accompanying claims.

REFERENCE EXAMPLE 1

Preparation of α-tocopheryl succinic acid

In a 500 ml rounded-flask, 10 g of dl-α-tocopherol was dissolved in 200 ml of acetone. Thereto was 2.79 g of succinic anhydride and 2.8 g of triethylamine added at temperature of 30° C. and was stirred for 4 hours at the same temperature. After the termination of the reaction, the mixture was concentrated, and the residue was then dissolved in ethyl acetate. Organic layer was washed twice with diluted hydrochloric acid solution and three times with water. Then organic layer was separated, dried and concentrated under reduced pressure. Thereto was petroleum ether added, and then the mixture was stayed overnight to produce solid material. The formed solid material was filtered and dried, to give 10 g of the title compound as white powder(yield: 80%).

REFERENCE EXAMPLE 2
Preparation of δ-tocopheryl succinic acid
In a 500 ml rounded-flask, 10 g of dl-δ-tocopherol was dissolved in 200 ml of acetone. Thereto was 2.98 g of succinic anhydride and 3.0 g of triethylamine added at temperature of 30° C. and was stirred for 4 hours at the same temperature. After the termination of the reaction, the mixture was concentrated, and the residue was then dissolved in ethyl acetate. Organic layer was washed twice with diluted hydrochloric acid solution and three times with water. Then organic layer was separated, dried and concentrated under reduced pressure. Thereto was petroleum ether added, and then the mixture was stayed overnight to produce solid material. The formed solid material was filtered and dried, to give 8.66 g of the title compound as white powder(yield; 72%).

REFERENCE EXAMPLE 3
Preparation of γ-tocopheryl succinic acid
In a 500 ml rounded-flask, 10 g of dl-γ-tocopherol was dissolved in 200 ml of acetone. Thereto was added 2.88 g of succinic anhydride and 2.92 g of triethylamine at temperature of 30° C. and was stirred for 4 hours at the same temperature. After the termination of the reaction, the mixture was concentrated, and the residue was then dissolved in ethyl acetate. Organic layer was washed twice with diluted hydrochloric acid solution and three times with water. Then organic layer was separated, dried and concentrated under reduced pressure. Thereto was petroleum ether added, and then the mixture was stayed overnight to produce solid material. The formed solid material was filtered and dried, to give 8.91 g of the title compound as white powder(yield; 72%).

EXAMPLE 1
Preparation of 1,3 -bis(N-(2-hydroxyethyl)-α-tocopherylsuccinoylamino) -2-hydroxypropane:
Into a 500 ml rounded-flask, were introduced 4.5 g of N,N-dimethylformamide and 7.34 g of thionylchloride. The mixture was stirred well for 30 minutes, and the solution of 31.22 g of α-tocopheryl succinic acid(Reference Example 1) in 50 ml of tetrahydrofurane was added dropwise. The mixture was stirred for 2 hours at room temperature, to give α- tocopheryl succinic acid chloride.
Into a 500 ml rounded-flask equipped with reflux condenser, were introduced 48.9 g of ethanolamine and 200 ml of ethanol. The mixture was stirred well, and 12.9 g of 1,3-dichloro-2-hydroxypropane was added dropwise for 1 hour. The mixture was refluxed for 4 hours and then cooled to room temperature. Thereto was added 56 g of solution of 10% KOH/ethanol to produce precipitates, which were removed by filtration. The solvent and unreacted ethanolamine were evaporated off under reduced pressure, and the residue was recrystallized from ethanol and chloroform. The product was filtered and dried under reduced pressure to give 13.1 g of N,N'-bis(2-hydroxyethyl)-2-hydroxy-1,3-propanediamine.
Into other 500 ml rounded-flask, were introduced 6.0 g of magnesium oxide and 20 g of distilled water. The mixture was stirred. Thereto was added 5.0 g of N,N'-bis(2-hydroxyethyl)-2-hydroxy-1,3-propanediamine prepared above and 80 ml of tetrahydrofurane. α-tocopheryl succinic acid chloride prepared above was gradually added dropwise to the resulting mixture for 1 hour under violent stirring at room temperature. After stirring for 2 hours, the mixture was filtered, then the residue was washed with 200 ml of chloroform. The filtrates and washed solution were mixed. Then organic layer was separated, dried and concentrated, to give 23.0 g of the title compound as a white solid, which was identified by IR and NMR. The results are shown in Table 1.

EXAMPLE 2
Preparation of 1,3-bis(N-(2-hydroxyethyl)-δ-tocopherylsuccinoylamino) -2-hydroxypropane:
The procedure described in Example 1 was followed by employing 29.0 g of δ-tocopherylsuccinic acid, instead of α-tocopherylsuccinic acid of Example 1, to give 20.7 g of the title compound as a white solid, which was identified by IR and NMR. The results are shown in Table 1.

EXAMPLE 3
Preparation of 1,3-bis(N-(2-hydroxyethyl)-γ-tocopherylsuccinoylamino)-2-hydroxypropane:
The procedure described in Example 1 was followed by employing 30.4 g of γ-tocopherylsuccinic acid, instead of α-tocopherylsuccinic acid of Example 1, to give 23.65 g of the title compound as a white solid, which was identified by IR and NMR. The results are shown in Table 1.

EXAMPLE 4
Preparation of phosphate diester of 1,3-bis(N-(2-hydroxyethyl)-α-tocopheralsuccinoylamino)-2-hydroxypropane;
Into 250 ml three necked-flask, 5.0 g of 1,3-bis(N-(2-hydroxyethyl)-α-tocopherylsuccinoylamino)-2-hydroxypropane and 100 ml of 1,2-dichloroethane were placed under stirring to be dissolved. The mixture was cooled to 10~15° C. in an ice bath, added dropwise the solution of 17 g of phosphorus oxychloride in 50 ml of 1,2-dichloroethane, the temperature of the solution was kept at 10~15° C.
After the addition, the mixture was stirred for 1~2 hours. Distilled water was added, and stirred violently. The organic phase was separated and washed twice with distilled water. The organic phase was dried over magnesium sulfate, then the solvent was removed under reduced pressure to give 4.5 g of the title compound.

EXAMPLE 5
Preparation of phosphate diester of 1,3-bis(N-(2-hydroxyethyl)-δ-tocopherylsuccinoylamino)-2-hydroxypropane;
This compound was prepared according to the procedure of Example 4 using the 7.0 g of 1,3-bis(N-(2-hydroxyethyl)-δ-tocopherylsuccinoylamino)-2-hydroxypropane and 2.2 g of phosphorous oxychloride. The yield of title compound was 6.8 g.

EXAMPLE 6
Preparation of sulfate diester of 1,3-bis(N-(2-hydroxyethyl)-δ-tocopherylsuccinoylamino)-2-hydroxypropane;
This compound was prepared according to the procedure of Example 4 using the 5.0 g of 1,3-bis(N-(2-hydroxyethyl)-γ-tocopherylsuccinoylamino)-2-hydroxypropane and 1.2 g of sulfonic chloride. The yield of title compound was 4.6 g.

EXAMPLES 7~9
Preparation of salts of compounds of Examples 4 to 6
Each of the compounds prepared in Examples 4 to 6 was dissolved in ethanol, and an ethanol solution containing NaOH in an equivalent concentration corresponding to phosphoric group or sulfuric group contained in the compound was added dropwise under stirring to neutralize. After neutralization, the resulting salts were filtered and dried.

TABLE 1

| Compounds | $^1$H-NMR($\delta$, ppm) | IR (cm$^{-1}$; C=O) | $^{13}$C-NMR (ppm; C=O) |
|---|---|---|---|
| Ex. 1 | 0.85(24H, s), 1.14~1.50(48H, m), 1.85(4H, m), 1.96(6H, s), 2.04(6H, s), 2.07(6H, s), 2.57(4H, t), 2.85(4H, t), 2.95(4H, t), 3.18(4H, m), 3.48(4H, m), 3.65(4H, m) | 1645 | 171 |
| Ex. 2 | 0.88(12H, s), 1.14~1.51(24H, m), 1.85(2H, m), 2.04(3H, s), 2.56(2H, t), 2.86(2H, t), 2.95(2H, t), 3.18(4H, m), 3.48(4H, m), 3.65(4H, m) | 1620 | 170 |
| Ex. 3 | 0.85(12H, s), 1.14~1.50(24H, m), 1.85(2H, m), 2.04(6H, s), 2.07(6H, s), 2.56(2H, t), 2.84(2H, t), 2.95(2H, t), 3.48(4H, m), 3.67(4H, m) | 1645 | 172 |

EXPERIMENTAL EXAMPLE 1

The solubility of a natural ceramide and of ceramide-like compounds:

Ceramide Type 3 represented by the following formula (III) has been mainly used in cosmetics. Accordingly, in this experiment were compared solubility of the ceramide Type 3 (obtained from bovine brain) and the ceramide-like compounds of Examples 1 to 3 in various solvents such as ethanol, which have been widely used in cosmetics. Samples were dissolved in the solvents of 80° C. then cooled to 20° C. The results are shown in Table 2.

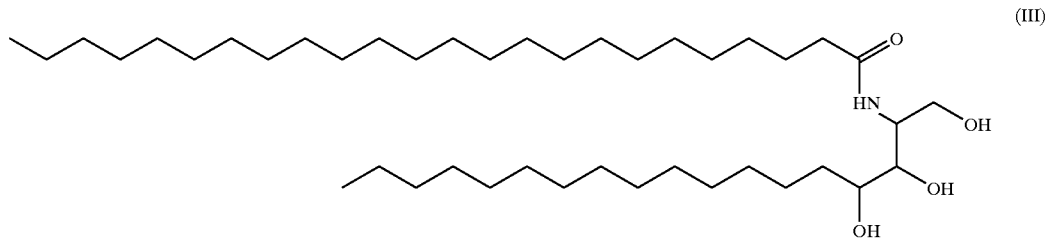

(III)

TABLE 2

(wt/wt %, 20° C.)

| | Solvents | | | | |
|---|---|---|---|---|---|
| Compounds | Ethanol | Octyl dodecanol | Octyl Palmitate | Isopropyl palmitate | Cetyl octanoate |
| Natural Ceramide (type 3) | <1% | <1% | <1% | <1% | <1% |
| Ex. 1 | >5% | >5% | >5% | >5% | >5% |
| Ex. 2 | >5% | >5% | >5% | >5% | >5% |
| Ex. 3 | >5% | >5% | >5% | >5% | >5% |

Formulations 1~3 and Comparative Formulations 1~2
Cream

Organic phase and water phase were separately mixed and heated. Two mixtures were mixed together and then emulsified under a stirring. The mixture was cooled to room temperature, to give a cream.

| | C. Formulations | | Formulations | | |
|---|---|---|---|---|---|
| Materials | 1 | 2 | 1 | 2 | 3 |
| Cetostearyl alcohol | 1.0 | 1.0 | 1.0 | 1.0 | 1.0 |
| Lipophilic monostearic glycerine | 1.0 | 1.0 | 1.0 | 1.0 | 1.0 |
| Monostearic polyoxyethylene glycerine | 1.5 | 1.5 | 1.5 | 1.5 | 1.5 |
| Self-emulsified monostearic glycerine | 1.0 | 1.0 | 1.0 | 1.0 | 1.0 |
| Caprylic/capric tryglyceride | 6.0 | 6.0 | 6.0 | 6.0 | 6.0 |
| Liquid paraffin | 6.0 | 6.0 | 6.0 | 6.0 | 6.0 |
| Squalane | 4.0 | 4.0 | 4.0 | 4.0 | 4.0 |
| Tocopheryl acetate | 0.5 | 0.5 | 0.5 | 0.5 | 0.5 |
| Natural ceramide of Type 3 | — | 1.0 | — | — | — |
| Sodium salt of compound of Example 1 | — | — | 1.0 | — | — |
| Sodium salt of compound of Example 2 | — | — | — | 1.0 | — |
| Sodium salt of compound of Example 3 | — | — | — | — | 1.0 |
| Stearic acid | 0.5 | 0.5 | 0.5 | 0.5 | 0.5 |
| Cholesterol | 0.7 | 0.7 | 0.7 | 0.7 | 0.7 |
| Alantoin | 0.4 | 0.4 | 0.4 | 0.4 | 0.4 |
| Glycine | 0.5 | 0.5 | 0.5 | 0.5 | 0.5 |

-continued

| Materials | C. Formulations | | Formulations | | |
|---|---|---|---|---|---|
| | 1 | 2 | 1 | 2 | 3 |
| Glycerine | 7.0 | 7.0 | 7.0 | 7.0 | 7.0 |
| 1,3-Butyleneglycol | 7.0 | 7.0 | 7.0 | 7.0 | 7.0 |
| Xantan gum | 0.5 | 0.5 | 0.5 | 0.5 | 0.5 |
| Placenta extracts | 1.0 | 1.0 | 1.0 | 1.0 | 1.0 |
| Hyaruronic acid extracts | 1.0 | 1.0 | 1.0 | 1.0 | 1.0 |
| Green tea extracts | 1.0 | 1.0 | 1.0 | 1.0 | 1.0 |
| Preservative | q.s. | q.s. | q.s. | q.s. | q.s. |
| Perfume | q.s. | q.s. | q.s. | q.s. | q.s. |
| Distilled water | to 100 | to 100 | to 100 | to 100 | to 100 |

EXPERIMENTAL EXAMPLE 2

Human Patch Test: Safety onto the Skin

In order to evaluate the safety of cosmetic compositions containing the ceramide-like compounds onto the facial skin, the conventional patch test was carried out for cream prepared in Formulations 1~3 and Comparative Formulations 1~2 in seven (7) groups consisting of five(5) of healthy male or female for 10 days, and the level of skin irritation was estimated according to the following scoring system:

4 Extremely severe irritation, estimated to be inadequate as a cosmetic
3 Severe irritation, estimated to be better not to use as a cosmetic
2 A little irritation, estimated to be carefully used as a cosmetic
1 Little irritation
0 No irritation, estimated to be adequate for the sensitive skin

TABLE 3

| Material | C. Formulations | | Formulations | | |
|---|---|---|---|---|---|
| | 1 | 2 | 1 | 2 | 3 |
| Scores | 0.3 | 0.3 | 0.2 | 0.5 | 0.3 |

As shown in Table 3, there is no significant difference in skin irritation, compared with control. Therefore, it is estimated that the ceramide-like compounds of the present invention are a safe material for topical application on the skin.

EXPERIMENTAL EXAMPLE 3

Skin recuperation

In order to evaluate the skin recuperation of the cosmetic compositions containing the ceramide-like compounds, acetone was used as skin damaging material and cream prepared in Formulations 1~3 and Comparative Formulations 1~2 were used as a curative material. And, skin recuperation was evaluated by measuring TEWL (transepidermal water loss) with Evaporimeter.

The test was carried out for 7 groups consisting of five(5) of hairless guinea pigs. The pig'rib was treated with acetone for 30 minutes using Finn chamber. After removing the acetone patch, 200 µl of each test material of the composition prepared in Formulations 1~3 and Comparative Formulations 1~2 was applied.

Measurement of TEWL was carried before treatment, 30 min, 1 hour, 2 hours, 4 hours, 6 hours and 8 hours after acetone treatment. The results are shown in Table 4. The score is calculated by considering TEWL measured before acetone treatment as "0" the TEWL measured immediately after removing the acetone patch as "100".

TABLE 4

Unit: AU

| | | Immediately after removing acetone patch | After removing acetone patch | | | | | |
|---|---|---|---|---|---|---|---|---|
| | | | 30 min | 1 hour | 2 hours | 4 hours | 6 hours | 8 hours |
| C. Formulations | 1 | 100 | 98 | 95 | 92 | 82 | 80 | 77 |
| | 2 | 100 | 118 | 131 | 91 | 78 | 58 | 51 |
| Formulations | 1 | 100 | 104 | 110 | 63 | 55 | 40 | 33 |
| | 2 | 100 | 99 | 97 | 65 | 55 | 41 | 30 |
| | 3 | 100 | 101 | 102 | 68 | 58 | 49 | 42 |

As shown in Tables 4, compared with the composition containing no ceramide derivatives, the compositions containing the ceramide-like compounds of the present invention are significantly effective in skin recuperation ability.

EXPERIMENTAL EXAMPLE 4

Skin protection

In order to evaluate the protection action of the cosmetic compositions containing the ceramide-like compounds, acetone was used as an irritant and compositions prepared in the Formulations 1~3 and Comparative Formulations 1~2 were used as a curative material.

The test was carried out for 7 groups consisting of five(5) of hairless guinea pigs for 7 days. The pig's rib was treated with 2.5% of SDS(sodium dodecylsulfate) for 30 minutes using Finn chamber. After removing the SDS patch, 200 µl of each test material of the composition prepared in Formulations 1~3 and Comparative Formulations 1~2 was applied. Measurement of TEWL was carried before treatment, 1 hour and 24 hours after SDS treatment. The results are shown in Table 5.

TABLE 5

Unit: AU

| | | Before SDS patch | After removing SDS patch | |
|---|---|---|---|---|
| | | | 1 hr | 24 hrs |
| C. Formulations | 1 | 10 | 25 | 19 |
| | 2 | 10 | 23 | 15 |
| Formulations | 1 | 10 | 16 | 12 |
| | 2 | 10 | 14 | 11 |
| | 3 | 10 | 17 | 12 |

As shown in Tables 5, compared with the composition containing no ceramide derivatives, the compositions containing the ceramide-like compounds of the present invention are significantly effective in protective action against external irritation

EXPERIMENTAL EXAMPLE 5

Anti-oxidative activity

Anti-oxidative activity was evaluated for compounds prepared in Examples 1 to 3 according to the following two method. Also, this experiment was applied to vitamin E and vitamin E acetate in order to compare the activities.

EXPERIMENTAL EXAMPLE 5-1

Anti-oxidative activity using DPPH

Diphenylpicrylhydrazyl(DPPH) has been known as a radical reaction inhibitor which is stabilized by the radical reaction. Also, it has a chromophoric property with compounds having anti-oxidative activity. Therefore, this experiment utilized the above property.

About 50 ml of DPPH was introduced into the test tube. And samples were added dropwise thereto. After addition, the test tube was maintained in constant temperature bath of 37° C. for 30 minutes. The extent of color development was measured by UV spectrophotometer. The results are shown in Table 6.

EXPERIMENTAL EXAMPLE 5-2

Anti-oxidative activity using linoleic acid

Linoleic acid is easily oxidized to be peroxide due to double bond contained therein. Therefore, this experiment utilized the above property.

The control solution employed in this experiment was prepared by adding 2.88 ml of 2.5% linoeic acid in ethanol and 9 ml of 40 mmol phosphate buffer(pH 7.0) to 200 ml of ethanol. This control solution was maintained in the dark of 40° C. And, sample solutions were prepared by adding 9.7 ml of 75% ethanol, 0.1 ml of 30% ammoniumthiocyanate and 0.1 ml of each sample, to 0.1 ml of the control solution. After 3 minutes, the absorbance was measured at 500 nm by using a UV spectrophotometer. Lower absorbance value means higher anti-oxidative activity. The results are shown in Table 6.

TABLE 6

| Sample | Experiment Example 5-1 | Experiment Example 5-2 |
|---|---|---|
| Control | — | 0.17 |
| Compound of Example 1 | Brown | 0.23 |
| Compound of Example 2 | Brown | 0.29 |
| Compound of Example 3 | Brown | 0.30 |
| Vitamin E | No color change | 0.23 |
| Vitamin E acetate | No color change | 0.44 |

Based on the results of the above experimental examples, the compositions containing the ceramide-like compounds of the present invention as an active ingredient will be exemplified in the form of various formulations. It is expected that the composition can increase moisture retention, skin tonicity and recuperation ability, and may protect the skin from the external irritations, thereby deferring skin aging effectively.

Formulation 4 Skin softeners

| Materials | Formulation 32 |
|---|---|
| Sodium salt of Compound of Example 1 | 0.2 |
| Cholesterol | 0.7 |
| Glycerine | 3.0 |
| 1,3-Butyleneglycol | 1.0 |
| Cellulose gum | 0.1 |
| Ethanol | 10.0 |
| POE-16 octyldodecylether | 0.2 |
| Polysorbate-60 | 0.2 |
| Preservative | q.s. |
| Pigments | q.s. |
| Perfume | q.s. |
| Distilled water | to 100 |

Formulation 5 Nutrient toilet waters

| Materials | Formulation 5 |
|---|---|
| Sodium salt of compound of Example 2 | 1.0 |
| Stearic acid | 0.7 |
| Cholesterol | 1.0 |
| Cetostearyl alcohol | 0.7 |
| Polysorbate-60 | 1.5 |
| Sorbitan sesqioleate | 0.5 |
| Liquid paraffin | 5.0 |
| Squalane | 5.0 |
| Glycerine | 5.0 |
| Carboxyvinyl polymer | 0.1 |
| Triethanolamine | 0.12 |
| Preservative | q.s. |
| Pigments | q.s. |
| Perfume | q.s. |
| Distilled water | to 100 |

Formulation 6 Nutrient creams

| Materials | Formulation 6 |
|---|---|
| Sodium salt of compound of Example 3 | 3.0 |
| Cholesterol | 5.0 |
| Cetostearyl alcohol | 3.0 |
| Stearic acid | 2.0 |
| Polysorbate-60 | 1.5 |
| Sorbitan sesqioleate | 0.5 |
| Liquid paraffin | 10.0 |
| Squalane | 10.0 |
| Glycerine | 6.0 |
| Triethanolamine | 0.5 |
| Preservative | q.s. |
| Pigments | q.s. |
| Perfume | q.s. |
| Distilled water | to 100 |

Formulation 7 Essences

| Materials | Formulation 7 |
|---|---|
| Compound of Example 1 | 1.0 |
| Myristic acid | 5.0 |

13

-continued

| Materials | Formulation 7 |
|---|---|
| Cholesterol | 7.0 |
| Cetostearyl alcohol | 1.0 |
| Glycerine | 15.0 |
| 1,3-Butyleneglycol | 4.0 |
| Cellulose gum | 0.1 |
| Hyaruronic acid extracts | 10.0 |
| Carboxyvinyl polymer | 0.12 |
| Triethanolamine | 0.17 |
| Ethanol | 3.0 |
| Polysorbate-60 | 0.2 |
| POE-25 octyldodecylether | 0.2 |
| Preservative | q.s. |
| Pigments | q.s. |
| Perfume | q.s. |
| Distilled water | to 100 |

Formulation 8

Cleansing foams

| Materials | Formulation 8 |
|---|---|
| Compound of Example 5 | 2.0 |
| Cholesterol | 5.0 |
| Beeswax | 1.0 |
| Stearic acid | 5.0 |
| Polysorbate-60 | 0.5 |
| Myristic acid | 26.0 |
| KOH | 5.0 |
| Glycerine | 6.0 |
| EDTA-4Na | 0.2 |
| Pigments | q.s. |
| Perfume | q.s. |
| Distilled water | to 100 |

Formulation 9 Packs

| Materials | Formulation 9 |
|---|---|
| Sodium salt of compound of Example 6 | 3.0 |
| Cholesterol | 0.7 |
| Polyvinyl alcohol | 14.0 |
| Cellulose gum | 0.1 |
| Glycerine | 1.0 |
| PEG 4000 | 1.0 |
| POE-16 octyldodecylether | 0.4 |
| Ethanol | 6.0 |
| Preservative | q.s. |
| Pigments | q.s. |
| Perfume | q.s. |
| Distilled water | to 100 |

What is claimed is:

1. A compound represented by the following general formula (I):

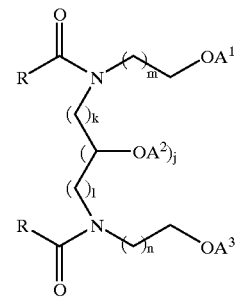

wherein, m and n, which may be the same or different, each is independently an integer from 1 to 3, inclusive;

k and l, which may be the same or different, each is independently an integer from 1 to 2, inclusive;

j is 0 or 1;

$OA^1$, $OA^2$ and $OA^3$, which may be the same or different, each represents OH or any one of the following structures:

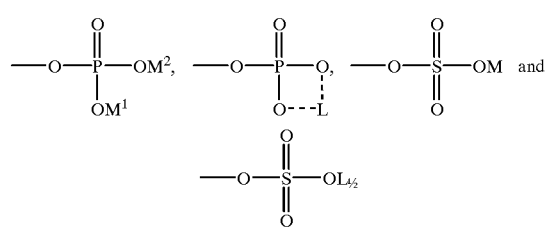

(wherein,

M, $M^1$ and $M^2$ represent independently alkali metals or organic base containing nitrogen, and L represents alkaline earth metals;

R represents a group having following structure:

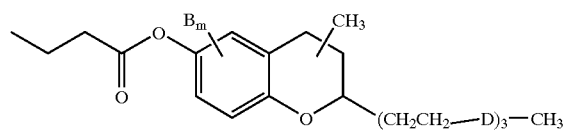

wherein,

B is methyl group at the 5-, 7- or 8-position;

m is an integer from 1 to 3, inclusive; and

D is $-CH_2-CH(CH_3)-$ or $-CH=C(CH_3)-$.

2. A method for preparing said compound (I) of claim 1, which comprises steps of:

(1) reacting a primary amino alcohol with a dihalo compound or a monohalo epoxy compound in alcohol under an inert atmosphere, to produce a secondary amino alcohol derivative represented by the Formula (II):

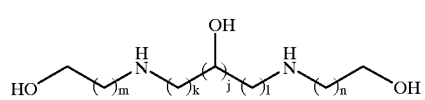

wherein, j, k, l, m and n have the same meanings as defined in said formula (I), respectively;

(2) reacting secondary amino alcohol derivative of step (1) with tocopherylsuccinic acid chloride in the presence of an alkali or organic base, to produce a diamide compound; and (3) dissolving said diamide compound of said step (2) in an organic solvent, and filtering off precipitates, and the recrystallizing a product from an organic solvent.

3. The method according to claim 2, wherein the primary amino alcohol of step (1) is selected from the group consisting of ethanolamine, 3-amino-1-propanol and 4-amino-1-butanol.

4. The method according to claim 2, wherein the dihalo compound of step (1) is selected from the group consisting of 1,3-dichloro-2-propanol, 1,3-dibromo-1-propanol, 1,2-dibromoethane and 1,2-dichloroethane; and monohalo epoxy compound of step (1) is selected from the group consisting of epichlorohydrin, epibromohydrin, 3,4-epoxy-1-chlorobutane, and 3,4-epoxy-1-bromobutane.

5. The method according to claim 2, wherein the alkali catalyst of step (2) is selected from the group consisting of potassium hydroxide, sodium hydroxide, magnesium hydroxide, calcium hydroxide, sodium carbonate, potassium carbonate, magnesium oxide and calcium oxide; and the organic base catalyst of step (2) is selected from the group consisting of triethanolamine and pyridine.

6. The method according to claim 2, wherein the organic solvent of step (3) is one or more selected from the group consisting of methanol, ethanol, propanol, isopropanol, dichloromethane, chloroform, 1,2-dichloroethane, carbon tetrachloride, n-hexane, cyclohexane, benzene and toluene.

7. The method according to claim 2, which further comprises steps of (4) phosphorylating or sulfating said diamide compound obtained in step (3); and (5) neutralizing the product of the step (4) with alkali or base.

8. The method according to claim 7, wherein the phosphorylating reagent of step (4) is selected from the group consisting of phosphorus oxychloride and phosphoric anhydride.

9. The method according to claim 7, wherein the sulfating reagent of step (4) is selected from the group consisting of chlorosulfonic acid and sulfur trioxide.

10. The method according to claim 7, wherein the neutralizing agent employed in step (5) is selected from the group consisting of alkali metal oxides, alkali earth metal oxides, basic amino acids, ammonia or amine, cationic polymers and cationic surfactants.

11. The method according to claim 10, wherein the alkali metal oxides are selected from the group consisting of sodium hydroxide and potassium hydroxide.

12. The method according to claim 10, wherein the alkali earth metal oxides are selected from the group consisting of calcium hydroxide, magnesium hydroxide, calcium oxide and magnesium oxide.

13. The method according to claim 10, wherein the basic amino acids are selected from the group consisting of lysine, arginine and histidine.

14. The method according to claim 10, wherein the amine is triethanolamine.

15. The method according to claim 10, wherein the cationic polymers are selected from the group consisting of polyquaternium-4, polyquaternium-6, polyquaternium-7, polyquaternium-10, polyquaternium-11 and polyquaternium-16.

16. The method according to claim 10, wherein the cationic surfactants are lauryldimethylbenzylammonium chloride and stearyldimethylbenzylammonium chloride.

17. A cosmetic composition containing compound (I) claimed in claim 1.

18. The cosmetic composition according to claim 17, which the compound is contained in an amount of 0.001~20% by weight.

* * * * *